(12) United States Patent
Coyle

(10) Patent No.: US 7,344,515 B2
(45) Date of Patent: Mar. 18, 2008

(54) GUIDING CATHETER WITH EMBOLIC PROTECTION BY PROXIMAL OCCLUSION

(75) Inventor: James Coyle, Somerville, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 355 days.

(21) Appl. No.: 10/944,313

(22) Filed: Sep. 17, 2004

(65) Prior Publication Data

US 2006/0064058 A1 Mar. 23, 2006

(51) Int. Cl.
*A61M 29/00* (2006.01)

(52) U.S. Cl. .......... 604/104; 604/95.04; 604/509; 606/194

(58) Field of Classification Search ........ 604/508–509, 604/95.03, 95.04, 99.01, 96.01, 103.03, 103.14, 604/104–109, 528, 530, 103, 103.04, 103.06, 604/103.09; 606/191, 194; 600/585
See application file for complete search history.

(56) References Cited

U.S. PATENT DOCUMENTS

| 4,572,186 A | 2/1986 | Gould et al. |
|---|---|---|
| 4,650,472 A | 3/1987 | Bates |
| 5,120,323 A | 6/1992 | Shockey et al. |
| 5,542,926 A * | 8/1996 | Crocker ............... 604/102.02 |
| 5,669,881 A | 9/1997 | Dunshee |
| 5,725,512 A | 3/1998 | Swartz et al. |
| 5,759,173 A | 6/1998 | Preissman et al. |
| 5,910,129 A * | 6/1999 | Koblish et al. ........ 604/95.03 |
| 5,922,009 A | 7/1999 | Epstein et al. |
| 6,056,770 A | 5/2000 | Epstein et al. |
| 6,221,086 B1 | 4/2001 | Forber |
| 6,312,407 B1 | 11/2001 | Zadno-Azizi et al. |
| 6,413,235 B1 | 7/2002 | Parodi |
| 6,425,909 B1 | 7/2002 | Dieck et al. |
| 6,461,346 B1 | 10/2002 | Buelna |
| 6,464,712 B1 * | 10/2002 | Epstein et al. ............ 606/213 |
| 6,595,952 B2 | 7/2003 | Forsberg |
| 6,635,068 B1 | 10/2003 | Dubrul et al. |
| 2002/0026145 A1 * | 2/2002 | Bagaoisan et al. ....... 604/96.01 |

FOREIGN PATENT DOCUMENTS

| WO | WO99/15223 | 4/1999 |
|---|---|---|
| WO | WO01/17589 | 3/2001 |

* cited by examiner

*Primary Examiner*—Nicholas Lucchesi
*Assistant Examiner*—Theodore J Stigell
(74) *Attorney, Agent, or Firm*—James F. Crittenden (57) ABSTRACT

A guiding catheter includes an elongate shaft with a central lumen and a mechanically expandable sealing membrane mounted about the distal end of the shaft. An expansion wire is slidably disposed in a dedicated lumen within the catheter, the expansion wire having an expandable distal portion with a pre-formed expanded shape capable of expanding the sealing membrane into sealing engagement with the wall of an artery to provide occlusion of blood flowing through the artery. In one embodiment, a steering wire is slidably disposed in a dedicated lumen within the catheter and is fixed adjacent the shaft distal end. Pushing or pulling the steering wire deflects the distal end of the catheter. In another embodiment, the guiding catheter has a pre-formed curve adjacent the distal end of the shaft.

31 Claims, 6 Drawing Sheets

GUIDING CATHETER WITH EMBOLIC PROTECTION BY PROXIMAL OCCLUSION

FIELD OF THE INVENTION

The present invention relates generally to an intraluminal guiding catheter used in a medical procedure, and more particularly, to a guiding catheter with embolic protection by proximal occlusion.

BACKGROUND OF THE INVENTION

Stenosis, or narrowing of a blood vessel such as a coronary artery may comprise a hard, calcified substance and/or a softer thrombus material. There have been numerous therapeutic procedures developed for the treatment of stenosis in a coronary artery. One of the better-known procedures is percutaneous transluminal coronary angioplasty (PTCA). According to this procedure, the narrowing in the artery can be reduced by positioning a dilatation balloon across the stenosis and inflating the balloon to re-establish acceptable blood flow through the artery. Additional therapeutic procedures may include stent deployment, atherectomy, and thrombectomy, which are well known and have proven effective in the treatment of such stenotic lesions.

The therapeutic procedure starts with the introduction of a guiding catheter into the cardiovascular system from a convenient vascular access location, such as through the femoral artery in the groin area or other locations in the arm or neck. The guiding catheter is advanced through the arteries until its distal end is located near the stenosis that is targeted for treatment. During PTCA, the distal end of the guiding catheter is typically inserted only into the ostium, or origin of the coronary artery. A guidewire is advanced through a central lumen in the guiding catheter and positioned across the stenosis. A therapy device, such as balloon dilatation catheter, is then slid over the guidewire until the dilatation balloon is properly positioned across the stenosis. The balloon is inflated to dilate the artery. To help prevent the artery from re-closing, a physician can implant a stent inside the artery. The stent is usually delivered to the artery in a compressed shape on a stent delivery catheter and expanded by a balloon to a larger diameter for implantation against the arterial wall.

Recently, a variety of devices have been developed to address atheroembolization, which is the obstruction of blood vessels by stenotic debris released during interventional catheterization therapies such as those mentioned above. Distal protection devices (DPDs) such as filters and occluders represent one class of intravascular devices that can be used to prevent atheroembolization. A filter mounted on a guidewire or a catheter may be positioned distally of a stenotic lesion to capture and remove potentially embolic debris without causing hemostasis. Alternatively, an occluder device may be positioned distally of a stenotic lesion to temporarily stop the flow of blood, including any stenotic debris that may have become entrained in the blood. The contaminated blood is aspirated from the treated area before the occluder device is collapsed to permit resumption of blood flow.

Occlusion devices may also be placed proximally of a stenotic lesion to provide so-called proximal protection. Proximal occlusion devices may be used alone to prevent atheroembolization, or they may be used in conjunction with a distal occluder to form an isolated treatment chamber about the lesion to be treated. Preliminary deployment of a proximal occlusion device may be advantageous in preventing atheroembolization because advancing a treatment catheter into a tight stenosis can dislodge particulate debris; even before the stenosis is being opened.

One type of guiding catheter that may be utilized is described in U.S. Patent Appn. No. 2002/0026145 A1 entitled "Method and Apparatus for Emboli Containment" to Bagaoisan et al. ("Bagaoisan"). Typical of most guiding catheters, the Bagaoisan catheter is pre-curved at the distal end to set and hold a supporting position in the vasculature while the therapeutic catheter crosses and treats the lesion. Additionally, the Bagaoisan catheter includes an expandable sealing balloon disposed around the guiding catheter's distal end that, when appropriately positioned, may be inflated to provide embolic protection by proximal occlusion.

Known occluder devices typically employ an inflatable occlusion balloon with its attendant expansion apparatuses, which may make the system cumbersome to prepare and use. Additionally, multi-catheter systems used to form isolated treatment chambers may be complex to use when it is desirable for the physician to work quickly to minimize the duration of hemostasis. Thus, a need exists for a guiding catheter having an atheroembolization prevention system that may be activated and deactivated simply and quickly during interventional catheterization procedures. Other desirable features and characteristics of the present invention will become apparent from the subsequent detailed description and the appended claims taken in conjunction with the accompanying drawings.

BRIEF SUMMARY OF THE INVENTION

The invention provides a guiding catheter with embolic protection by artery occlusion. In one embodiment, the guiding catheter includes a flexible shaft having a central lumen and an expandable sealing member mounted near the distal end of the flexible shaft. An expansion wire is slidably disposed within the flexible shaft and includes an expandable distal portion comprising a shape memory material that is pre-formed in the shape of a plurality of expanded coils. The expansion wire is used to expand the sealing member when the guiding catheter is positioned in the artery. The expansion wire is movable between a first non-expanded position and a second expanded position. The first non-expanded position is used while the guiding catheter is maneuvered through the patient's vasculature and the second expanded position is used to expand the sealing member into sealing engagement with the wall of the artery to provide proximal occlusion of blood flowing there through. The guiding catheter may also include an actuation assembly having an expansion actuation reel connected to the expansion wire.

In other embodiments of the invention, one or more steering wires may be slidably disposed in dedicated lumens within the guiding catheter, the steering wires being fixed to the catheter distal end. The guiding catheter may also include an actuation assembly having one or more steering actuation reels connected to the steering wires. Tension applied to the steering wire(s) causes deflection in a distal region of the guiding catheter, thus deforming the relatively straight or pre-curved shape of the catheter. The deformed shape may assist in "steering" the guiding catheter through a patient's vasculature, or the altered shape may provide a more stable, secure position during advancement of therapeutic devices, as when forcing a deflated angioplasty balloon through a tight stenosis, for example.

A method is disclosed for using the inventive guiding catheter with embolic protection by artery occlusion. The method includes providing a guiding catheter having one or more of the embodiments described above; inserting the guiding catheter into the vascular system of the patient and positioning the expandable sealing member proximal to the stenotic lesion to be treated; and moving the expansion wire to the second position to expand the sealing member into sealing engagement with the wall of the artery to provide proximal occlusion of blood flow.

In other embodiments of the invention, the method may also include: inserting a therapeutic device through the central lumen of the guiding catheter; positioning the therapeutic portion of the therapeutic device across the stenosis; and treating the stenosis with the therapeutic device.

BRIEF DESCRIPTION OF THE DRAWINGS

The following drawings are illustrative of particular embodiments of the invention and therefore do not limit its scope. They are presented to assist in providing a proper understanding of the invention. The drawings are not to scale and are intended for use in conjunction with the explanations in the following detailed descriptions. Like reference numerals denote like elements in the drawings, wherein.

DETAILED DESCRIPTION OF THE INVENTION

The following detailed description is merely exemplary in nature and is not intended to limit the invention or the application and uses of the invention. Although the description of the invention is in the context of protection against atheroembolization during treatment of blood vessels such as the coronary, carotid and renal arteries, the invention may also be used in any other passageways where it is deemed useful to provide temporary occlusion to block fluid flow. Furthermore, there is no intention to be bound by any expressed or implied theory presented in the preceding technical field, background, brief summary or the following detailed description.

Figures 1, 2:
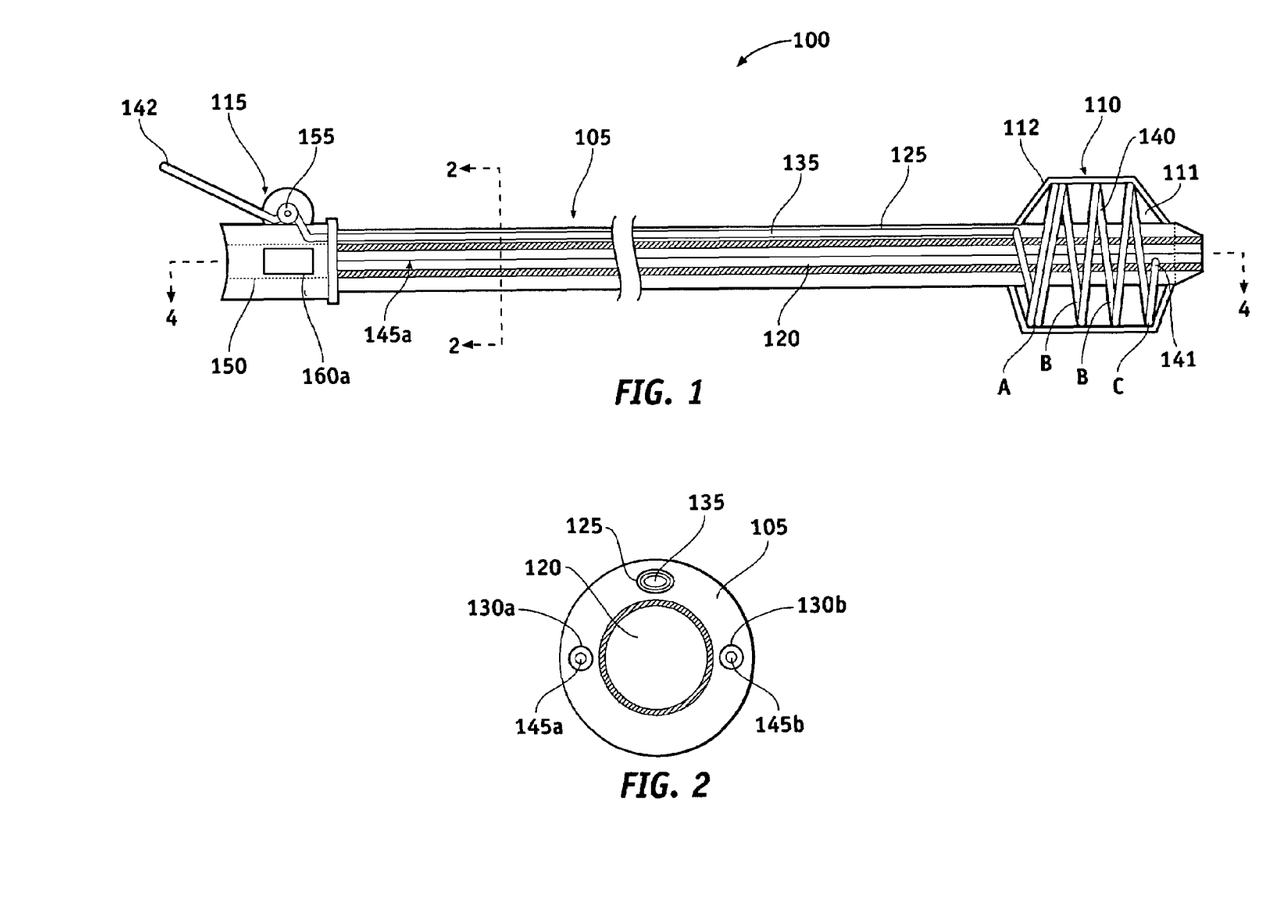
FIG. 1 is a longitudinal sectional view showing one embodiment of a guiding catheter in accordance with the invention, shown with a sealing member in an expanded configuration.
FIG. 2 is a cross-sectional view of the guiding catheter shown in FIG. 1, taken along line 2-2.

FIG. 1 is a longitudinal cross-sectional view showing one embodiment of a guiding catheter 100 in a deployed condition, and FIG. 2 shows a cross-sectional view taken along line 2-2 of FIG. 1. Guiding catheter 100 includes catheter shaft 105, sealing member 110 adjacent a distal end of the catheter shaft and actuation assembly 115 adjacent a proximal end of the catheter shaft. Catheter shaft 105 is a multi-lumen shaft having central lumen 120 and outer lumens 125, 130a and 130b. Central or "primary" lumen 120 is made of a low-friction material and is adapted to receive and guide a therapeutic medical device, such as a balloon catheter, a stent delivery system or other treatment device, to the desired location. The outer or "secondary" lumens include expansion wire lumen 125 and steering wire lumens 130a and 130b. Each of the lumens have wires slidably disposed within them, the wires being used to control the expansion/contraction of sealing member 110 or the steering of guiding catheter 100, as will be described in further detail below.

Catheter shaft 105 is a flexible shaft that is designed to advance through a patient's vasculature to remote arterial locations without buckling or undesirable bending. As is well known to those of skill in the art, catheter shaft 105 may include a pre-formed distal curve (not shown) that can aid in traversing a patient's vasculature, or can provide enhanced "backup support" as therapeutic catheters are advanced through lumen 120 of guiding catheter 100 and across a stenosis. Catheter shaft 105 may be constructed of one or more flexible biocompatible materials, including, but not limited to, polyethylene, polypropylene, polyurethane, polyesters, or PEBAX® polyethylene block amide copolymer (ELF Atochem, Philadelphia, Pa., U.S.A.). Catheter shaft 105 may also include a layer of braided filaments that resist kinking and enhance longitudinal transmission of rotation. To further aid in advancing guiding catheter 100 through the patient's vasculature, it may be desirable to vary the stiffness of catheter shaft 105 by varying the braid pitch, by varying the properties of materials used in construction, or by combining both techniques. The distal end of catheter shaft 105 may include a soft tip formed thereon via any of numerous methods know to those skilled in the art.

Sealing member 110 is mounted adjacent the distal end of catheter shaft 105 and is radially expandable to form sealing engagement with the artery or vessel wall. Sealing member 110 includes sealing member interior 111 that is in communication with expansion wire lumen 125. Sealing member 110 has sufficient flexibility such that when it is activated or expanded it will seal the artery or desired vessel and when it is contracted or deactivated it will lie snugly against the surface of catheter shaft 105. Sealing member 110 may be formed from an elastic material such as styrene-ethylene-butylene-styrene (SEBS), silicone, latex, or an elastomer. Alternatively, sealing member 110 may be made of an inelastic, flexible biocompatible polymer. Sealing member 110 may be attached to shaft 105 by any suitable manner known in the art, such as adhesive bonding or heat bonding.

Figure 3:
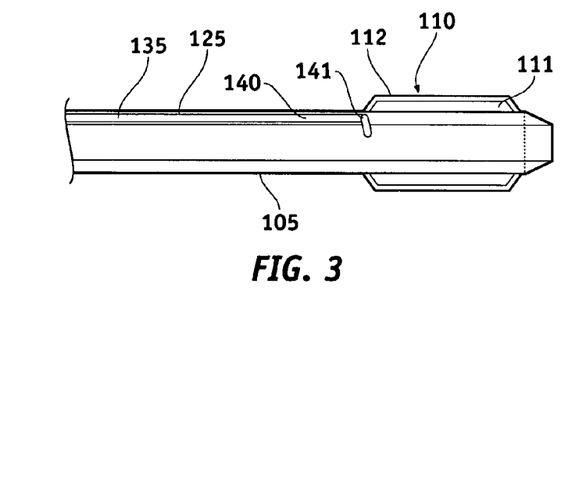
FIG. 3 is a side view of a distal portion of the guiding catheter of FIG. 1, shown with the sealing member in a contracted configuration.

Expansion wire 135 is slidably disposed in expansion wire lumen 125, and includes proximal portion 142 that may be coupled to actuation assembly 115 and expandable distal portion 140 that can move into and out of sealing member interior 111. Expandable distal portion 140 has a normally expanded shape and may have an expanded configuration such as a helical, ellipsoidal or biconical shape. While inside expansion wire lumen 125, expandable distal portion 140 is constrained in an unexpanded configuration, as shown in FIG. 3. When expandable distal portion 140 is extended distally beyond expansion wire lumen 125 and into sealing member interior 111, expandable distal portion 140 assumes its normally expanded configuration, thereby expanding sealing member 110, as shown in FIG. 1. The interior surfaces of expansion wire lumen 125 may be formed from, or coated with, a slippery or low-friction material, such as high-density polyethylene (HDPE) or polytetrafluoroethylene (PTFE).

Expandable distal portion 140 may be constructed of a shape memory material having the ability to recover an original pre-formed shape after being temporarily straightened or constrained, and also having the strength to expand sealing member 110. Expansion wire 135 may be made from nitinol (TiNi), stainless steel, or high-modulus plastic or other suitable shape memory material. Expansion wire 135 may have any cross-sectional shape, such as circular, oval or flat ribbon. In one embodiment, expansion wire 135 is a unitary filament with the desired expanded shape heat set directly into expandable distal portion 140. In an alternative embodiment, expandable distal portion 140 can be separately manufactured and pre-formed, then attached to expansion wire 135 by soldering, welding or other suitable joining means. In one embodiment, expandable distal portion 140 is made of the same material as the remainder of expansion wire 135. In another embodiment, expandable distal portion 140 is made a material that is different from the remainder of expansion wire 135.

Figure 4:
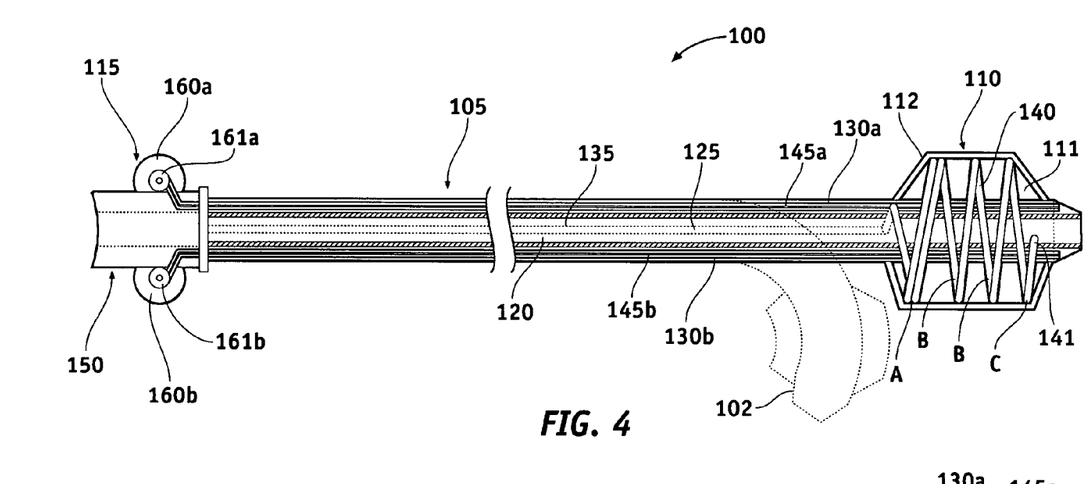
FIG. 4 is a longitudinal sectional view of the guiding catheter shown in FIG. 1, taken along line 4-4.

FIG. 4 is a longitudinal sectional view taken along line 4-4 in FIG. 1 and showing the actuation mechanism for steering guiding catheter 100. Guiding catheter 100 may be substantially straight, or guiding catheter 100 may include curve 102, shown in phantom, proximate the distal region of guiding catheter 100. Any one of a number of pre-formed curve shapes may be incorporated into guiding catheter 100, such as Judkins-type or Amplatz-type curves, as non-limiting examples. Curve 102 may be pre-formed utilizing various known methods including, but not limited to, the method disclosed in U.S. Pat. No. 5,902,287 entitled "Guiding Catheter and Method of Making Same." A desired curve 102 may be manually created from a straight or pre-formed distal region of guiding catheter 100 by manipulation of one or more steering wires.

Figure 5:
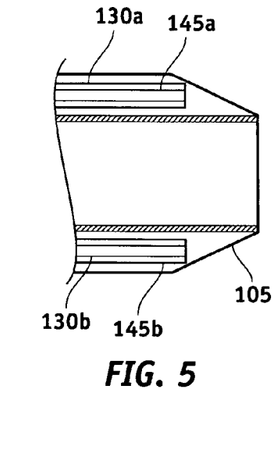
FIG. 5 is a close-up side view of the distal end of the guiding catheter shown in FIG. 1.

Steering wire lumens 130a and 130b extend along opposite sides of the shaft 105, and steering wires 145a and 145b are slidably disposed within steering wire lumens 130a and 130b, respectively. The distal ends of steering wires 145a and 145b are fixed or attached adjacent the distal end of shaft 105, as shown in FIG. 5. Proximal portions of steering wires 145a and 145b are coupled to the actuation assembly 115.

Actuation assembly 115, shown in FIGS. 1 and 4, includes hub 150, which may be attached to the proximal end of catheter shaft 105 by any temporary or permanent manner known to those skilled in the art. Hub 150 has a central opening in communication with central lumen 120 to allow passage of therapeutic devices there through. Actuation assembly 115 further includes expansion actuation reel 155 and steering actuation reels 160a and 160b. Actuation assembly 115 may be formed of a polymer or metal having the required hardness to also function as a port or a connector, i.e. a luer fitting. Hub 150 and actuation assembly 115 may be separately or integrally formed of medical grade polycarbonate, polyvinyl chloride, acrylic, acrylonitrile butadiene styrene (ABS), nylon or other rigid biocompatible material.

Expansion actuation reel 155 is part of actuation assembly 115, which is associated with hub 150, as shown in FIG. 1. Hub 150 includes inlet/outlet communication with expansion wire lumen 125, through which expansion wire 135 moves. Proximal portion 142 of expansion wire 135 may be threaded through the inlet and wound around actuation reel 155. In one configuration, proximal portion 142 is wound several turns around actuation reel 155 and the proximal end is left free to be manipulated by a user. To move expandable distal portion 140 into or out of membrane interior 111, actuation reel 150 is manually turned and expansion wire 135 is moved within expansion wire lumen 125. In alternative configurations, the longitudinal movement of expansion wire 135 within expansion wire lumen 125 may be manually controlled by a knob, a pinch roller system, a slider, or various other mechanisms suitable for the purpose.

Steering actuation reels 160a and 160b may be disposed within housings 161a and 161b, respectively, which are associated with hub 150, as shown in FIG. 4. Housings 161a and 161b include inlets/outlets that are in communication with steering wire lumens 130a and 130b through which steering wires 145a and 145b move. Proximal portions of steering wires 145a and 145b are coupled to steering actuation reels 160a and 160b, and the distal ends of steering wires 145a and 145b are fixed near the distal end of shaft 105. Rotation, or winding/unwinding action of one or both steering actuation reels 160a and 160b applies or releases tension to steering wires 145a and 145b, respectively to deflect or steer the distal end of guiding catheter 100.

Although steering wires 145a or 145b are illustrated herein as being coupled to actuation assembly 115 along with the expansion wire 135, it will be appreciated that a separate actuation mechanism or mechanisms may be used for steering wires 145a or 145b and expansion wire 135. Additionally, although some of the embodiments illustrate steering wire lumens 130a and 130 as being equally spaced apart from one another within shaft 105, it will be appreciated by those with skill that steering wire lumens 130 may be spaced apart from one another in any manner depending on a user's preference with regard to control of guiding catheter 100. Some embodiments may have only one steering wire within one steering wire lumen to deflect or steer catheter 100. In such an embodiment, steering may be accomplished by a combination of pushing and/or pulling the steering wire while twisting or rotating the catheter shaft in the desired direction. In other embodiments, it may be undesirable to twist or rotate the catheter shaft, in which case there may be more than two steering wire lumens with more than two steering wires employed to steer the catheter without rotation. Skilled artisans will also recognize that the terms "steer" and "steering," as used herein generally refer to various wires, lumens and actions causing deflection of the distal end of guiding catheter 100. However, it is to be understood that steering of guiding catheter 100 may include manual rotation of the catheter proximal end to cause rotation of the catheter distal end, with or without actions to cause simultaneous deflection of the distal end.

Figure 8:
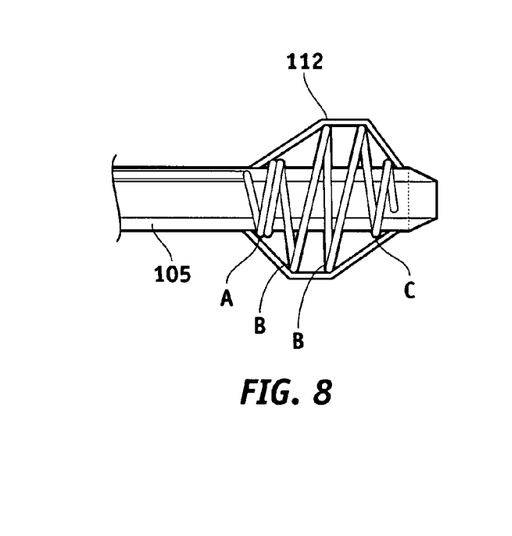
FIG. 8 is a distal longitudinal sectional view showing another embodiment of the expansion wire coils in accordance with the invention.
Figure 9:
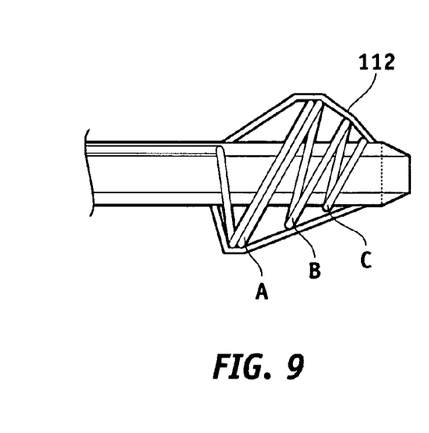
FIG. 9 is a distal longitudinal sectional view showing yet another embodiment of the expansion wire coils in accordance with the invention.

Expandable distal portion 140 of expansion wire 135 may be helical in shape and may include a predetermined number of coils formed therein. In one embodiment, expandable distal portion 140 includes coils A, B and C, which have substantially the same diameter, as shown in FIG. 1. In another embodiment, proximal and distal coils A and C comprise coils that are smaller in diameter than middle coils B, as shown in FIG. 8. In yet another embodiment, the proximal coil A has a larger diameter than middle coil B, which has a larger diameter than distal coil C, as shown in FIG. 9. Other variations of coil diameters may also be used. In still other embodiments, the coil diameter of expandable distal portion 140 may be a predetermined diameter to closely match the vessel diameter or shape. In this case, the user determines the vessel diameter and selects guiding catheter 100 such that sealing member 110 expands to substantially the same diameter as its predetermined, nominal coil diameter to match the vessel diameter without damaging the vessel. Such embodiments of guiding catheters having predetermined sealing member diameters may be appropriate for small vessels, unusually shaped vessels or exceptionally fragile vessels.

Figure 6:
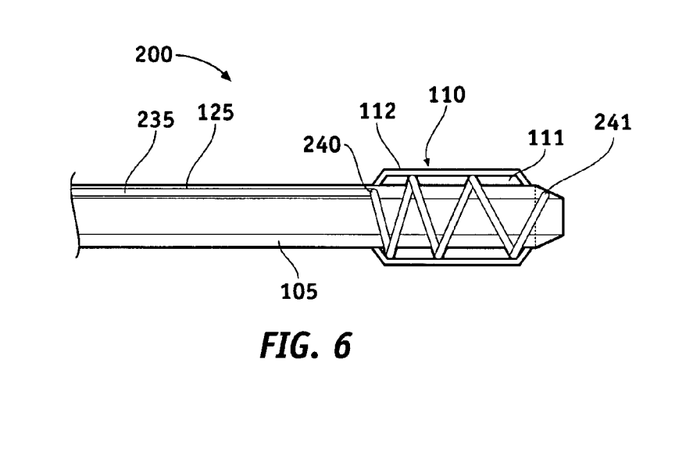
FIG. 6 is longitudinal sectional distal view of another embodiment of a guiding catheter in accordance with the invention, shown with a sealing member in a contracted configuration.
Figure 7:
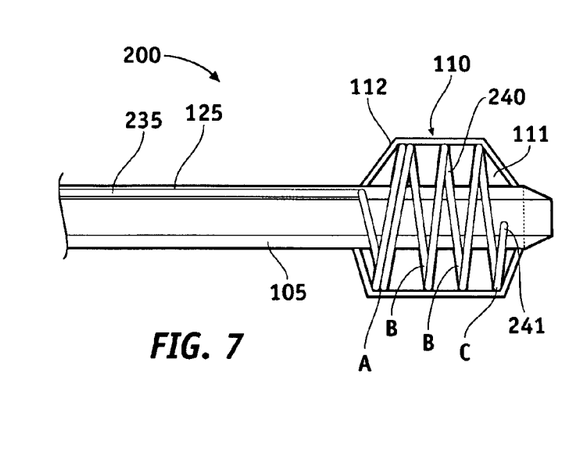
FIG. 7 is shows the embodiment of FIG. 6 with the sealing member in the expanded configuration.

FIG. 6 shows another embodiment of the invention that is similar in construction to guiding catheter 100 described above. In guiding catheter 200, expansion wire 235 is slidably disposed in expansion wire lumen 125. Expansion wire 235 includes expandable distal portion 240 that can expand and contract within sealing member interior 111, and a proximal portion that is coupled to actuation assembly 115. Distal portion 240 has a normally expanded configuration that may be, for example, helical, ellipsoidal or biconical in shape. Distal end 241 of expandable distal portion 240 is fixed near the distal end of catheter shaft 105. When expandable distal portion 240 is in the collapsed state, at least a portion of expandable distal portion 240 is disposed within sealing member interior 111 and is wrapped about catheter shaft 105. The remainder of expandable distal portion 240 is constrained in an unexpanded configuration inside expansion wire lumen 125. Advancing expansion wire 235 through expansion wire lumen 125 causes expandable distal portion 240 to unwrap from the catheter shaft and assume its normally expanded configuration. As the remainder of distal portion 240 continues to advance into sealing member interior 111, the expanded configuration of distal portion 240 fully deploys the sealing member 110, as shown in FIG. 7. Withdrawing expansion wire 235 wraps expandable distal portion 240 around catheter shaft 105, allowing sealing member 110 to collapse, as shown in FIG. 6.

Figure 10:
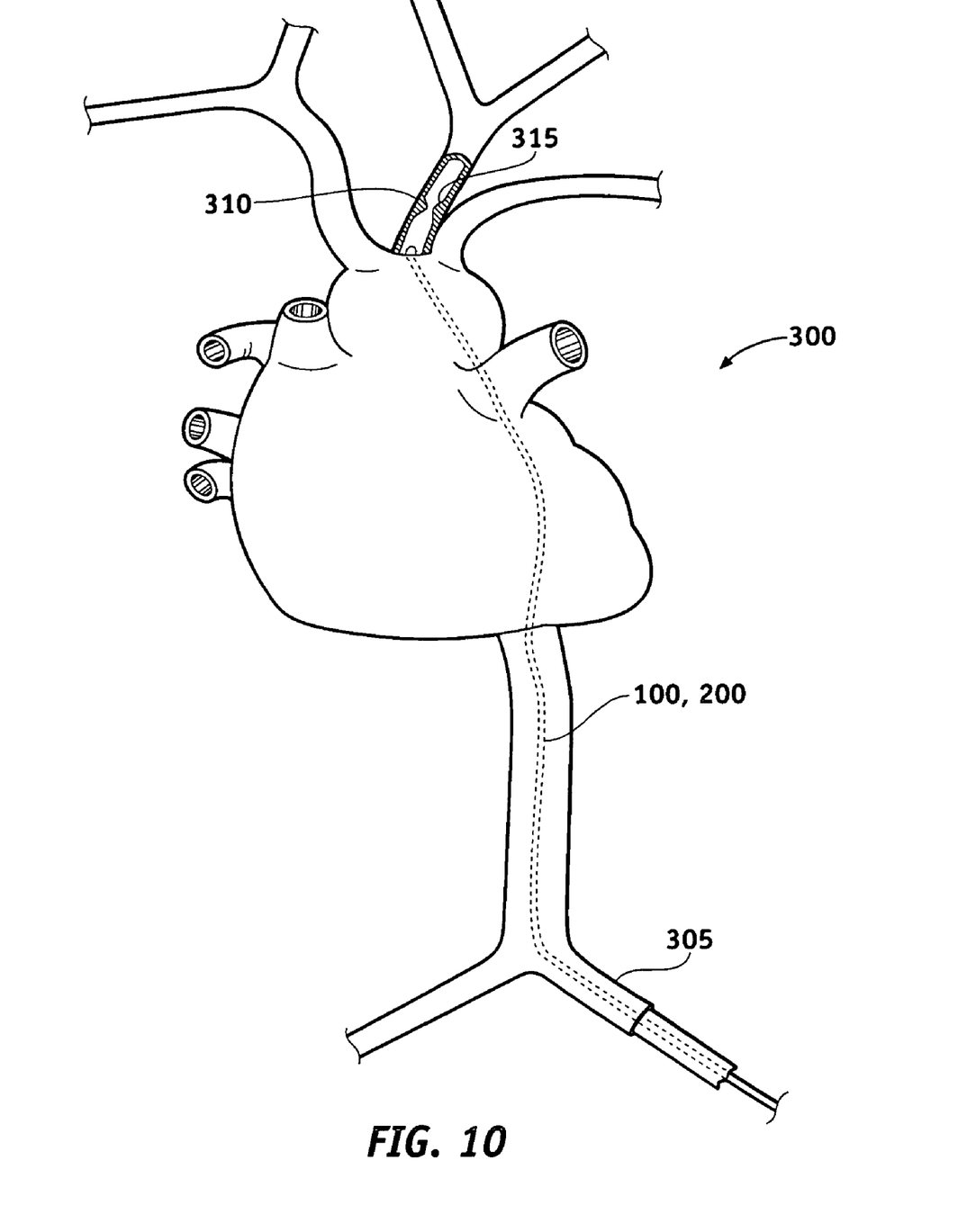
FIG. 10 is illustrates one embodiment of a guiding catheter in accordance with the invention, shown deployed in the cardiovascular system of a patient.

The operation and use of guiding catheter 100, 200 will now be described. FIG. 10 illustrates guiding catheter 100, 200 positioned within a patient's vascular system 300 for use with a therapeutic device. Guiding catheter 100, 200 is initially inserted into vascular system 300, typically through a femoral artery in the groin area. Guiding catheter 100, 200 is then advanced through aorta 305 until the distal end of the catheter is located near targeted artery 310. Optionally, guiding catheter 100, 200 may be advanced and steered through the patient's vasculature by deflecting the distal region of catheter 100, 200 using steering wires 145a and 145b, as described above. Guiding catheter 100, 200 is positioned such that the sealing member is located between the ostium of artery 310 and stenosis 315.

Figure 11:
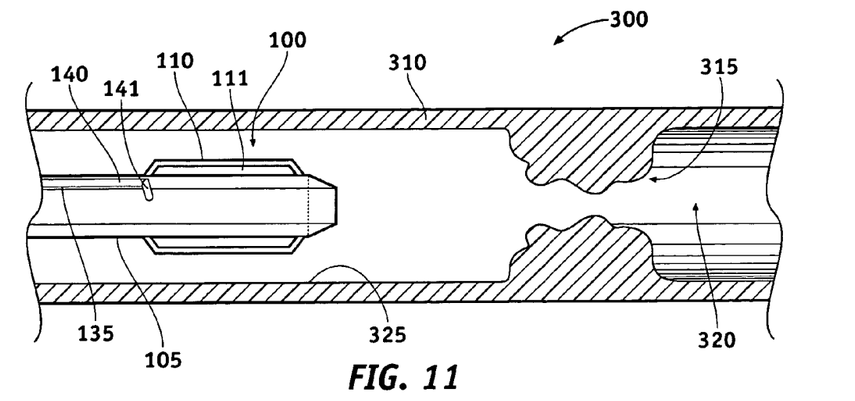
FIGS. 11-15 illustrate the deployment of an embodiment of the inventive guiding catheter in a diseased vessel during a typical angioplasty procedure.
Figure 12:
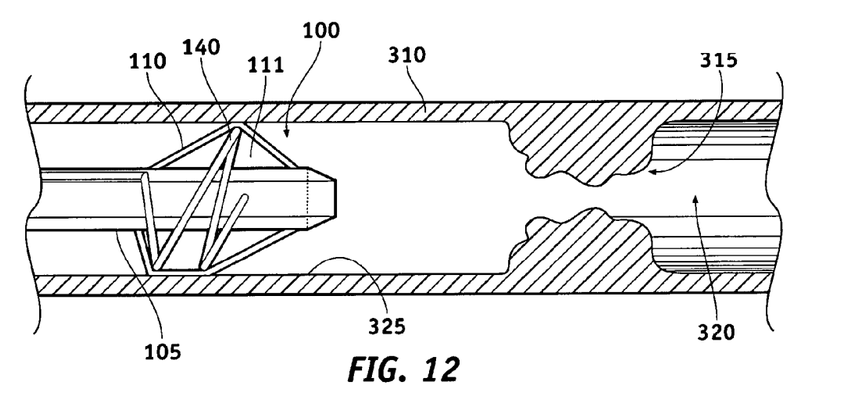

FIG. 11 shows the distal portion of guiding catheter 100 positioned in artery 310. The clinician then operates expansion actuation reel 155 (see FIG. 1) to advance expansion wire 135 through expansion wire lumen 125, causing wire distal end 141 and expandable distal portion 140 to exit expansion wire lumen 125 into sealing member interior 111, as shown in FIG. 12. As expansion wire 135 advances into sealing member interior 111, expandable distal portion 140 winds around the distal region of shaft 105 and reforms its original pre-formed shape, thereby expanding sealing member 110. Alternatively, in guiding catheter 200, wire distal end is fixed to shaft 105 and a proximal portion of expandable distal portion 240 is slidable within lumen 125, as shown in FIG. 6.

Figure 13:
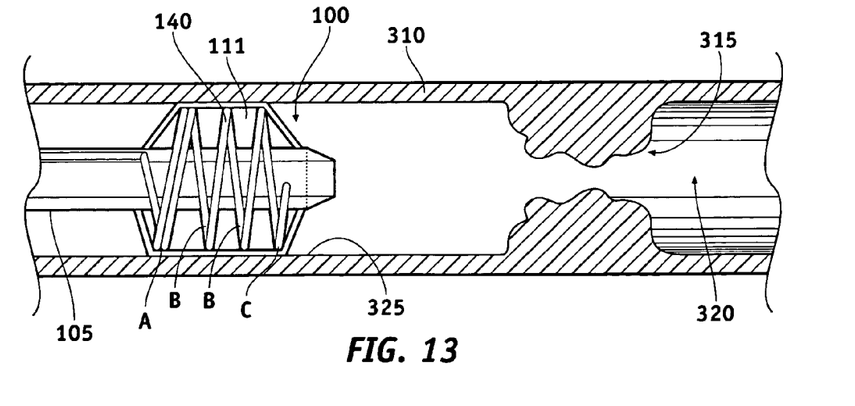

Next, as illustrated in FIG. 13, advancement of expansion wire 135 through expansion wire lumen 125 continues until expandable distal portion 140 has expanded sealing member 110 into sealing engagement with vessel wall 325 to provide proximal occlusion of blood flowing through artery 310. In one embodiment, expandable distal portion 140 has a helical shape with spring-like properties, and the helix diameter takes on the diameter of the vessel. In such an embodiment, expandable distal portion 140 applies mechanical pressure against the inner surface of sealing member 110, causing it to expand to the vessel diameter and into contact with vessel wall 325, sealing vessel lumen 320 proximal of stenosis 315.

Figure 14:
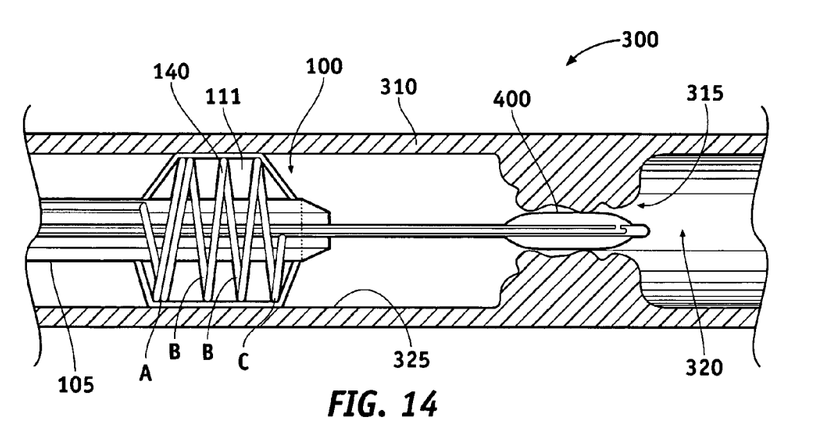
Figure 15:
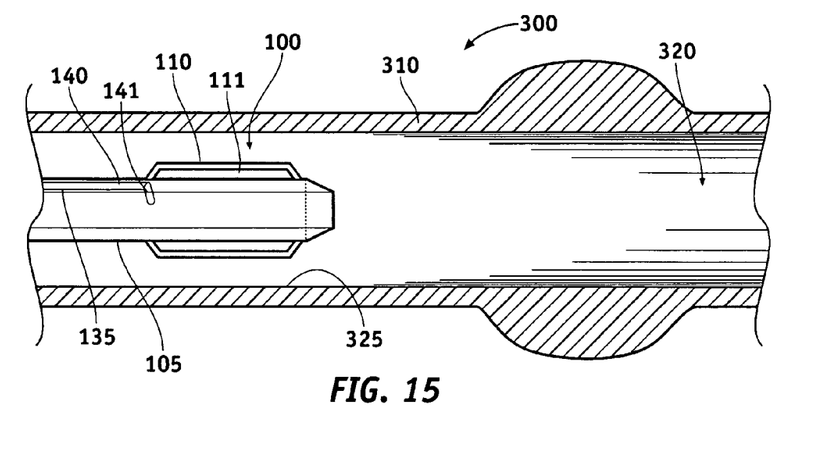

A therapeutic device, such as balloon dilatation catheter 400, including a dilatation balloon, is advanced through central lumen 120 until the balloon reaches a desired position within stenosis 315, as illustrated in FIG. 14. The dilatation balloon is then inflated to dilate the stenosis. Balloon dilatation catheter 400 may then be removed, and any debris present may be aspirated, either directly into guiding catheter 100 or, alternatively, into an aspiration catheter, which may be advanced to the treated area within vessel lumen 320. Then, sealing member 110 is collapsed as shown in FIG. 15, allowing blood flow to resume. Lastly, guiding catheter 100 is withdrawn from vessel lumen 320.

While at least one exemplary embodiment has been presented in the foregoing detailed description, it should be understood that various changes can be made in the function and arrangement of elements without departing from the scope of the invention as set forth in the appended claims and the legal equivalents thereof.

What is claimed is:

1. An endovascular guiding catheter having proximal embolic protection comprising:
    an elongate shaft having proximal and distal ends;
    a central, first lumen extending through the shaft between open proximal and distal ends, the first lumen being adapted to receive and guide an intravascular device to a location distally beyond the distal end of the shaft;
    a hub coupled to the shaft proximal end;
    an expandable sealing member having an interior and being mounted about the shaft distal end, the sealing member being expandable to a cross-section sufficient to occlude endovascular flow;
    a second lumen extending through the shaft and adapted to receive an expansion wire, the second lumen extending through the shaft and having a distal end in communication with the interior of the sealing member; and
    an expansion wire slidably disposed within the expansion wire lumen and protruding proximally therefrom, the expansion wire having an expandable distal portion with a pre-formed expanded shape to expand the sealing member to its occlusive cross-section, the expandable distal portion being movable between a non-expanded position and an expanded position, the expanded position being within the interior of the sealing member.

2. The guiding catheter of claim 1, wherein the distal portion of the expansion wire is maintained in the non-expanded position by containment within the expansion wire lumen.

3. The guiding catheter of claim 1, wherein the expandable wire further includes a distal end fixedly coupled adjacent the shaft distal end and, in the non-expanded position, the expandable distal portion partly positioned within the interior of the sealing member and partly positioned within the expansion wire lumen.

4. The guiding catheter of claim 3, wherein, in the expanded position, the entire expandable distal portion is positioned within the interior of the sealing member.

5. The guiding catheter of claim 4, wherein, in the expanded position, the expandable distal portion is capable of assuming the pre-formed expanded shape within the interior of the sealing member.

6. The guiding catheter of claim 1, wherein the expandable distal portion comprises a shape memory material.

7. The guiding catheter of claim 6, wherein the shape memory material is selected from the group consisting of nitinol (TiNi), stainless steel, and high-modulus plastic.

8. The guiding catheter of claim 1, wherein the pre-formed expanded shape comprises a plurality of coils.

9. The guiding catheter of claim 8, wherein one or more of the coils are sized to expand the sealing member.

10. The guiding catheter of claim 8, wherein the plurality of coils include proximal, distal and middle coils, each coil having a diameter.

11. The guiding catheter of claim 10, wherein the diameters of the proximal and distal coils are substantially similar to one another.

12. The guiding catheter of claim 10, wherein the diameter of the proximal coil is larger than the diameter of the distal coil.

13. The guiding catheter of claim 10, wherein the diameters of the proximal and distal coils are smaller than the diameter of the middle coil.

14. The guiding catheter of claim 10, wherein one or more of the coils are sized to expand the expandable sealing member into sealing engagement with a vessel to be occluded.

15. The guiding catheter of claim 1, further comprising an expansion actuation reel rotatably mounted on the hub, the expansion wire being movably coupled to the expansion actuation reel.

16. The guiding catheter of claim 1, further comprising a curved shape pre-formed in the shaft adjacent the shaft distal end.

17. The guiding catheter of claim 1, further comprising: at least one steering wire lumen extending through the shaft; and at least one steering wire slidably disposed within the at least one steering wire lumen and protruding proximally there from, a distal end of the at least one steering wire being fixedly coupled adjacent the shaft distal end.

18. The guiding catheter of claim 17, further comprising at least one steering actuation reel rotatably mounted on the hub, the at least one steering wire being movably coupled to the at least one steering actuation reel.

19. The guiding catheter of claim 17, wherein two or more steering wire lumens are spaced about the central lumen in the shaft.

20. The guiding catheter of claim 1, wherein the shaft is comprises a biocompatible material selected from the group consisting of polyamide, polyester, polyethylene, polypropylene, polyurethane, and polyethylene block amide copolymer.

21. The guiding catheter of claim 1, wherein the sealing member is formed from a biocompatible elastic material.

22. The guiding catheter of claim 21, wherein the elastic material is selected from the group consisting of styrene-ethylene-butylene-styrene (SEBS), silicone, latex, and an elastomer.

23. The guiding catheter of claim 1, wherein the sealing member is made of an inelastic, flexible biocompatible polymer.

24. The guiding catheter of claim 1, wherein the sealing member is attached to the shaft by adhesive or heat bonding.

25. A guiding catheter with embolic protection by proximal occlusion, comprising:
    an elongate shaft having proximal and distal ends;
    a central lumen extending through the shaft between open proximal and distal ends; a hub coupled to the shaft proximal end;
    an expandable sealing member having an interior and being mounted about the shaft distal end;
    an expansion wire lumen extending through the shaft and being in communication with the interior of the sealing member; and
    an expansion wire slidably disposed within the expansion wire lumen and protruding proximally there from, the expansion wire having an expandable distal portion with a pre-formed expanded shape, the expandable distal portion being movable between a non-expanded position and an expanded position, the expanded position being within the interior of the sealing member;
    at least one steering wire lumen extending through the shaft; and
    at least one steering wire slidably disposed within the at least one steering wire lumen and protruding proximally there from, a distal end of the at least one steering wire being fixedly coupled adjacent the shaft distal end.

26. The guiding catheter of claim 25, wherein the central lumen is adapted to receive a medical device.

27. A method of using a guiding catheter with embolic protection during a therapeutic procedure on a patient, the method comprising:
    providing a guiding catheter comprising an elongate shaft having a central lumen there through, an expansion wire lumen, an expandable sealing member mounted about a shaft distal end, the expansion wire lumen being in communication with an interior of the sealing member, an expansion wire having an expandable distal portion with a pre-formed expanded shape, the expansion wire being slidably disposed within the expansion wire lumen, the expandable distal portion being movable between a non-expanded position and a expanded position, the expanded position being inside the sealing member;
    inserting the guiding catheter into a vascular system of the patient;
    positioning the expandable sealing member in an artery proximal to a stenotic lesion to be treated; and
    moving the expandable distal portion to the expanded position to expand the sealing member into sealing engagement with a wall of the artery to provide occlusion of blood flowing there through.

28. The method of claim 27, wherein the guiding catheter further comprises a curved shape pre-formed in the shaft adjacent the shaft distal end.

29. The method of claim 27, wherein the guiding catheter further comprises one or more steering wires slidably disposed within one or more steering wire lumens, a distal end of each steering wire being fixedly coupled adjacent the shaft distal end; and wherein the method further comprises moving the one or more steering wires to deflect the shaft distal end.

30. The method of claim 27, further comprising: inserting a therapeutic device through the central lumen of the guiding catheter; positioning a therapeutic portion of the therapeutic device within the stenosis; and treating the stenosis with the therapeutic device.

31. The method if claim 30, wherein the therapeutic device is an angioplasty catheter and treating the stenosis is inflating a balloon to dilate the stenosis.

* * * * *